United States Patent [19]

Kase et al.

[11] Patent Number: 5,070,137

[45] Date of Patent: Dec. 3, 1991

[54] PROCESS FOR THE PREPARATION OF POLYISOCYANATE

[75] Inventors: Mitsuo Kase, Chiba; Yoichi Kawasaki, Ichihara; Noboru Okoshi, Sodegaura, all of Japan

[73] Assignee: Dainippon Ink and Chemicals, Inc., Tokyo, Japan

[21] Appl. No.: 382,876

[22] Filed: Jul. 21, 1989

[30] Foreign Application Priority Data

Jul. 22, 1988 [JP] Japan .................................. 63-181512

[51] Int. Cl.$^5$ ...................... C08L 75/00; C08G 18/08; C07D 487/12; C07D 251/32
[52] U.S. Cl. ........................................ 524/590; 528/49; 544/186; 544/221; 544/222
[58] Field of Search ................... 544/221, 186, 222; 528/49; 524/590

[56] References Cited

U.S. PATENT DOCUMENTS 4,582,888  4/1986  Kase et al. ............................. 528/49
4,789,705  12/1988  Kase et al. ............................ 524/590

FOREIGN PATENT DOCUMENTS 61-129173  6/1986  Japan .

*Primary Examiner*—Johann Richter

*Attorney, Agent, or Firm*—Armstrong, Nikaido, Marmelstein, Kubovcik & Murray

[57] ABSTRACT

Disclosed is a process for preparing isocyanurate-type polyisocyanates characterized by reacting an aliphatic or alicyclic diisocyanate compound comprising hexamethylene diisocyanate as a major component in the presence of an isocyanuration catalyst represented by general formula [I],

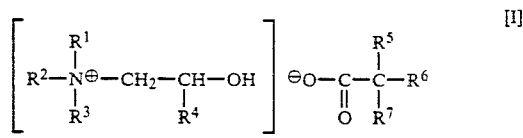

wherein $R^1$, $R^2$ and $R^3$ independently represent a hydrocarbon group containing 1 to 20 carbon atoms, or a hydrocarbon group containing one or more hetero atoms; at least two of $R^1$, $R^2$ and $R^3$ may be linked to each other; $R^4$ indicates a hydrogen atom or a hydrocarbon group containing 1 to 20 carbon atoms; and $R^5$, $R^6$ and $R^7$ independently represent a hydrocarbon group containing 1 to 20 carbon atoms. Diol-modified isocyanurate-type polyisocyanates can be prepared additionally using a hydrocarbon diol in the process.

10 Claims, No Drawings

PROCESS FOR THE PREPARATION OF POLYISOCYANATE

BACKGROUND OF THE INVENTION

This invention relates to a process for preparing polyisocyanates that can be used as a curing agent for two-pack urethane resins usable in the fields of paint, adhesives and molding materials.

More specifically, this invention relates to a process for preparing polyisocyanates of the isocyanurate type which is derived from a diisocyanate compound mainly composed of hexamethylene diisocyanate and which can be used as a curing agent for two-pack urethane resins.

The isocyanurate-type polyisocyanates, which are derived from hexamethylene diisocyanate through isocyanuration reaction, are important since they are more durable curing agents for two-pack urethane resins than conventional biuret-type or adduct-type polyisocyanates due to the high chemical stability of the isocyanurate ring contained therein.

Also, since the isocyanurate-type polyisocyanates have in the molecules no such bonds as urethane bonds which cause hydrogen bonding, they are considered good curing agents for two-pack urethane resins used in paints and adhesives due to their low viscosity and good dissolving power in various organic solvents.

However, in the process for preparing isocyanurate-type polyisocyanates with an isocyanuration catalyst, hexamethylene diisocyanate has different properties than those of aromatic diisocyanate compounds such as tolylene diisocyanate, indicating high selectivity for the catalyst and tending to involve side reactions, e.g., carbodiimide formation, that readily take place causing coloration or the like. Therefore, isocyanuration catalysts having particularly high performance are required in this process.

Furthermore, the isocyanurate-type polyisocyanates derived from hexamethylene diisocyanate when used as a curing agent for two-pack urethane resins are known to have somewhat poor compatibility with acrylic polyols which are widely used as a major component of the curing agent. Accordingly, to prepare isocyanurate-type polyisocyanates having improved compatibility with the acrylic polyols, they must be polyisocyanates which have a low molecular weight and in which the content of the compounds containing only a single isocyanurate ring (hereafter, referred to as "mononuclear" polyisocyanates or compounds) is high. That is why isocyanuration catalysts having improved performance are required.

However, since hexamethylene diisocyanate has high selectivity for catalysts, conventional isocyanuration catalysts (i.e., various tertiary amine compounds and phosphines) that are efficient for aromatic diisocyanate compounds such as tolylene diisocyanate cannot be used in the isocyanuration of hexamethylene diisocyanate. Accordingly, there has been an ongoing need to develop other efficient isocyanuration catalysts useful for the purpose.

As the results of extensive studies conducted recently on the catalysts useful in the isocyanuration of hexamethylene diisocyanate, N-(2-hydroxyalkyl)-quaternary ammonium aliphatic carboxylate was proposed as a catalyst with high catalytic activity. Japanese Patent Publication (Kokai) No. 55-143978 discloses use of the catalyst in amounts of from 200 to 1,000 ppm to prepare isocyanurate-type polyisocyanates. Although this process using a quaternary ammonium compound catalyst is more advanced when compared as the preceding proposals, the isocyanuration reaction performed using hexamethylene diisocyanate alone causes coloration of the resin due to accompanied side reactions, failing to provide isocyanurate-type polyisocyanates having a light color and acceptable quality.

Very recently, the present inventors have found in their study that N-(2-hydroxyalkyl)-quaternary ammonium aromatic carboxylate is an efficient isocyanuration catalyst with high activity (Japanese Patent Publication (Kokai) No. 60-181078). However, the process of the preceding proposals proved inadequate to suppress the coloration which occurred during the isocyanuration reaction when hexamethylene diisocyanate was used alone. Thus far, light color, high-quality isocyanurate-type polyisocyanates with a high content of a mononuclear polyisocyanate compound have been difficult to prepare at comparatively low conversions.

As previously mentioned, the conventional processes proved insufficient for preparing light color, high-quality isocyanurate-type polyisocyanates using hexamethylene diisocyanate alone.

SUMMARY OF THE INVENTION

In light of the above-mentioned situation, extensive research has been made with view to developing a catalyst that would effectively promote the isocyanuration reaction of hexamethylene diisocyanate, and as the result it has now been found that use of a specified isocyanuration catalyst is effective, thus completing the invention.

Therefore, this invention provides a process for preparing isocyanurate-type polyisocyanates characterized by reacting an aliphatic or alicyclic diisocyanate compound comprising hexamethylene diisocyanate as a major component in the presence of an isocyanuration catalyst represented by general formula [I],

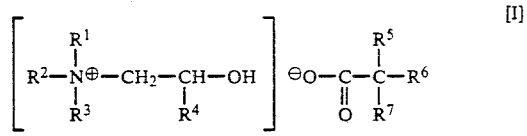

wherein $R^1$, $R^2$ and $R^3$ independently represent a hydrocarbon group containing 1 to 20 carbon atoms, or a hydrocarbon group containing one or more hetero atoms; at least two of $R^1$, $R^2$ and $R^3$ may be linked to each other; $R^4$ indicates a hydrogen atom or a hydrocarbon group containing 1 to 20 carbon atoms; and $R^5$, $R^6$ and $R^7$ independently represent a hydrocarbon group containing 1 to 20 carbon atoms.

Also, this invention provides a process for preparing diol-modified isocyanurate-type polyisocyanates characterized by reacting an aliphatic or alicyclic diisocyanate compound comprising hexamethylene diisocyanate as a major component in the presence of (a) an isocyanuration catalyst represented by general formula [I], wherein $R^1$, $R^2$ and $R^3$ independently represent a hydrocarbon group containing 1 to 20 carbon atoms, or a hydrocarbon group containing one or more hetero atoms; at least two of $R^1$, $R^2$ and $R^3$ may be linked to each other; $R^4$ indicates a hydrogen atom or a hydrocarbon group containing 1 to 20 carbon atoms;

and $R^5$, $R^6$ and $R^7$ independently represent a hydrocarbon group containing 1 to 20 carbon atoms, and (b) a hydrocarbon diol.

The processes of this invention are advantageous in that they can produce isocyanurate-type polyisocyanates which have a light color and high quality and are of a high industrial value using a small amount of catalyst since they use a catalyst having improved performance as compared with the conventional processes.

DETAILED DESCRIPTION OF THE INVENTION

In general formula [I] above, the hetero atom may be, for example, a nitrogen atom to which an alkyl group such as a methyl group may be attached.

The resulting isocyanurate-type polyisocyanates or diol-modified isocyanurate-type polyisocyanates contain preferably at least 65% by weight of a mononuclear polyisocyanate compound. When the content of the mononuclear polyisocyanate compound is below 65% by weight, the compound does not mix well.

Typical examples of the isocyanuration catalyst, i.e., N-(2-hydroxyalkyl)-quaternary ammonium tertiary aliphatic carboxylate represented by general formula [I] above as used in this invention include compounds with structures [Ia] to [Ik] shown below.

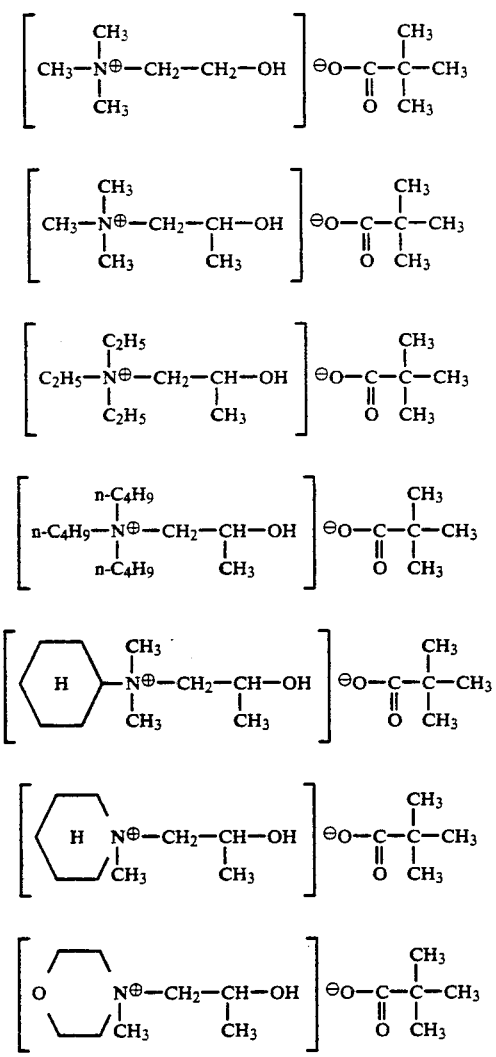

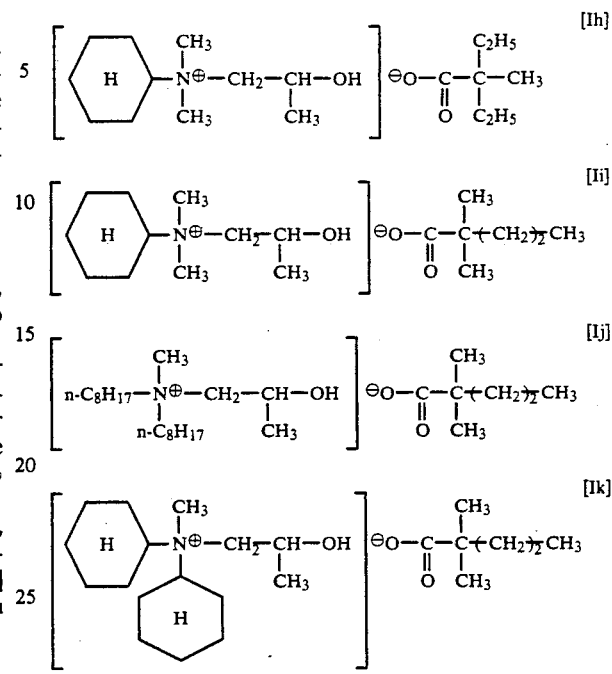

The compounds represented by general formula [I] and typically represented by formulae [Ia] to [Ik] above, are readily available through the established processes of Bechara or its modification as described in Japanese Patent Publication (Kokai) No. 52-17484.

The amount of the isocyanuration catalyst to be used is preferably from 20 to 200 ppm based on the weight of the charged diisocyanate compound which is mainly composed of hexamethylene diisocyanate. When the amount of the catalyst is smaller than 20 ppm, the reaction tends to proceed unsatisfactorily and on the other hand, the reaction tends to proceed excessively when the catalyst is used in an amount greater than 200 ppm and it will sometimes be difficult to control the reaction.

In general, the isocyanuration catalyst is used after diluting it with an organic solvent in which the catalyst is soluble. Dimethylacetamide, N-methylpyrrolidone or butyl Cellosolve acetate can be used as the solvent, and various kinds of alcohols such as ethyl alcohol, n-butyl alcohol, t-butyl alcohol, 2-ethylhexyl alcohol, benzyl alcohol, butyl Cellosolve, propylene glycol or 1,3-butanediol can be used.

For practical application of this invention, active hydrogen compounds such as alcohols, e.g., 1,3-butanediol and 2,2,4-trimethyl-1,3-pentandiol, and phenols, e.g., p-t-butylphenol and 2,6-dimethyl-4-t-butylphenol can be used as a co-catalyst.

Since the catalyst of this invention represented by general formula [I] above has a high catalytic activity, high-quality isocyanurate-type polyisocyanates can readily be obtained without using a co-catalyst. However, use of the above active hydrogen compounds as the co-catalyst will not depart from the scope of present invention.

The isocyanuration reaction of this invention normally proceeds at temperatures of from 30° to 120° C. The reaction at temperatures exceeding 120° C. is not favorable because the catalyst is deactivated or the quality of the product deteriorates as by coloration of polyisocyanate.

Since the isocyanuration catalyst represented by general formula [I] features high performance, the isocyanuration reaction of hexamethylene diisocyanate can be smoothly be promoted at the above temperatures (e.g., 60° C.). At the same time, the rate of formation of the isocyanurate-type polyisocyanates as the reaction proceeds can be evaluated by measuring the change in the refractive index of the reaction system. This is particularly effective and helpful in preparing low-molecular weight isocyanurate-type polyisocyanates with a high content of the mononuclear polyisocyanates.

Therefore, the conversion of the isocyanuration reaction is kept in the range of preferably from 8 to 65% by weight, and more preferably from 10 to 45% by weight, for obtaining isocyanurate-type polyisocyanates with a high content of the mononuclear polyisocyanates.

Thus, after the isocyanuration reaction, the isocyanuration catalyst used can be deactivated by using appropriate deactivators (e.g., acids such as dodecylbenzenesulfonic acid and monochloroacetic acid or organic acid halides such as benzoyl chloride).

Among the deactivators mentioned above, monochloroacetic acid is preferred since it can be refined with ease.

The isocyanurate-type polyisocyanates can readily be obtained by removing unreacted diisocyanate compounds from the reaction mixture containing the already deactivated catalyst using various types of molecular distillation still (e.g., rotary blade or rotary disc type).

The isocyanurate-type polyisocyanates resulting from hexamethylene diisocyanate are expressed by general formula [II] as follows:

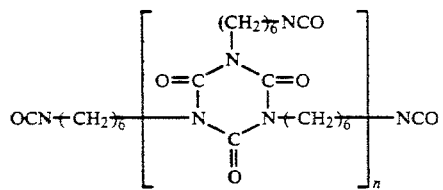

among which polyisocyanate compounds expressed by general formula [III], are composed of a mononuclear polyisocyanate in amounts of at least 65% by weight.

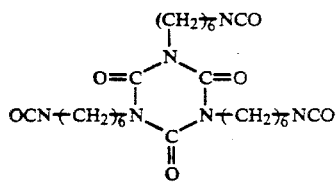

The resulting isocyanurate-type polyisocyanates can be used in their pure state or diluted state by using organic solvents such as toluene, xylene, ethyl acetate, butyl acetate or petroleum aromatic hydrocarbon solvents (e.g., Swasol 1000 produced by the Maruzene Petroleum Co.).

In the present invention, isocyanurate-type polyisocyanates obtained from hexamethylene diisocyanate as a major raw material are conceived as the primary subject. If desired, up to 40% by weight, preferably up to 30% by weight, of other raw materials such as aliphatic diisocyanate compounds, e.g., 2,2,4-trimethylhexamethylene diisocyanate and dodecamethylene diisocyanate or alicyclic diisocyanate compounds such as 1,4-cyclohexanediisocyanate and 1,3-bis(isocyanatomethyl)-cyclohexane can be added to the hexamethylene diisocyanate system.

In the process of preparing isocyanurate-type polyisocyanates according to this invention, hydrocarbon diols such as 1,3-butanediol, 1,6-hexanediol, 2,2,4-trimethyl-1,3-pentanediol, and cyclohexanedimethanol can if desired be used together with the catalyst in the isocyanuration reaction to prepare the diol-modified isocyanurate-type polyisocyanates. This process of preparing the modified type product is also included within the scope of the present invention. The amount of diol modification in the process of preparing the diol-modified isocyanurate-type polyisocyanates is preferably up to 30% by weight and more preferably up to 20%, based on the weight of the diisocyanate compound charged.

The isocyanurate-type polyisocyanates prepared according to the process of this invention play an important industrial role as a curing agent for polyurethane resins, and are particularly effective curing agents for use together with not only polyester polyol, which is a major ingredient of polyurethane resins but also acrylic polyol.

The acrylic polyol with a hydroxyl number of from 40 to 160 and a molecular weight of from 5,000 to 25,000 is commonly used, and modified acrylic polyol grafted with cellulose acetate butyrate (CAB) is also suitable for use in combination with the polyisocyanate used in this invention. In addition, fluoropolyol, which is soluble in organic solvents, can be used together with polyisocyanates obtained according to the process of this invention.

The polyisocyanates thus-obtained by the present invention in combination with the previously mentioned polyols can be applied to the fields of paint, adhesives, and molding materials.

EXAMPLES

This invention will be described in greater detail with reference to the following examples which are not construed as limiting this invention. All percentages are by weight unless otherwise indicated specifically.

EXAMPLE 1

A 5-liter four-necked glass flask (equipped with a stirrer, a nitrogen gas supply tube, an air cooling tube, and a thermometer) was charged with 3,500 g of hexamethylene diisocyanate (HDI) in a nitrogen gas atmosphere. While stirring, the temperature of the flask was raised to 55° C. in an oil bath, then a 20%-butyl Cellosolve solution of N,N,N-trimethyl-N-2-hydroxypropylammonium pivalate (molecular weight: 219), expressed by formula [1b] above, was added as an isocyanuration catalyst. When a total of 1.8 g of catalyst solution was added (103 ppm against charged HDI), the temperature inside the reactor rose to 63° C.

After the exothermic reaction ended, the reaction was constantly monitored by observing changes in the refractive index ($n_{25}D$) of the reaction mixture with controlling the temperature controlled at 60° C. When the refractive index of the reaction mixture reached 1.4625, 2.5 g of a 6.8%-xylene solution of monochloroacetic acid (molecular weight: 94.5) was added as a catalyst deactivator to terminate the reaction.

Then, the reaction mixture was cooled to room temperature. The deactivated reaction mixture had light color, indicating a Hazen color unit of 10 to 20.

Subsequently, a 1,000 g aliquot of the reaction mixture was subjected to molecular distillation to obtain 249.8 g (conversion: 25.0%) of polyisocyanate as a reaction residue, and 748.6 g (recovery ratio 75.0%) of HDI as a distillate.

The resulting polyisocyanate solution has a light color (Hazen color unit 40) and a Gardner viscosity at 25° C. (the same hereinafter) of W to X. The isocyanate group content (abbreviate as "NCO %") was 23.0%. The polyisocyanate (P-1) was confirmed to be an isocyanurate-type polyisocyanate from the infra-red absorption spectrum and 13C nuclear magnetic resonance spectrum analyses.

Also, the content of the product having a mononuclear polyisocyanate group in the molecule expressed by formula [III] above, which corresponded to general formula [II] in which n=1, was determined to be 70% using high-performance gel permeation chromatography, and the measured number-average molecular weight was 560.

The polyisocyanate (P-1) indicated good compatibility with acrylic polyol "ACRYDIC A-801" (produced by Dainippon Ink & Chemicals, Inc.; non-volatile content=50%, Gardner viscosity=P to T, acid value<3, hydroxyl number=50+2, solvent=toluene, butyl acetate) at an NCO/OH equivalent ratio of 1.0. When the resulting varnish was coated on a glass plate, a very cohesive, cured film was obtained.

Separately, a resin varnish was prepared by mixing the polyisocyanate solution with acrylic polyol (B) (glass transition temperature=50° C., non-volatile content=50%, molecular weight=15,000, acid value=1, hydroxyl number=50, solvent=butyl acetate), which was prepared in trial by using conventional radical polymerization from methyl methacrylate, styrene, ethyl acrylate, and β-hydroxyethyl methacrylate. When the resulting varnish was coated on a glass plate, a very cohesive, cured film was obtained.

EXAMPLE 2

The same procedure as described in Example 1 was performed except for the following. As the isocyanuration catalyst, a 20%-butyl Cellosolve solution of N,N,N-triethyl-N-2-hydroxypropylammonium pivalate (molecular weight 261), expressed by formula [1c] above, was introduced in a flask in portions. When a total of 1.6 g (91 ppm) of the catalyst solution was added, the temperature inside the reactor rose to 64° C. While maintaining the temperature at 60° C. when the refractive index of the reaction mixture reached 1,4625, 1.8 g of a 6.8%-xylene solution with monochloroacetic acid was added inside the reactor to terminate the reaction. The cooled reaction mixture had a light color with a Hazen color unit of 10.

Subsequently, a 1,000 g aliquot of the reaction mixture was subjected to molecular distillation to obtain 249.5 g (conversion 25.0%) of the aimed polyisocyanate as a reaction residue and, on the other hand, 750.2 g (recovery ratio 75.0%) of HDI as a distillate.

The resulting polyisocyanate (P-2) solution had a light color (Hazen color unit 30), Gardner viscosity of W, and NCO% of 23.3%. The polyisocyanate (P-2) was confirmed to be an isocyanurate-type polyisocyanate, containing 72% of the mononuclear polyisocyanate group with a number-average molecular weight of 540 (as determined through the same instrument analysis as in Example 1).

The polyisocyanate (P-2) indicated good compatibility with each of acrylic polyol: "ACRYDIC A-801" and the trial-made acrylic polyol (B). When the resulting varnish was coated on a glass plate, a very cohesive, cured film was obtained.

EXAMPLE 3

The same procedure as described in Example 1 was performed except for the following. As the isocyanuration catalyst, a 20%-butyl Cellosolve solution of N,N,N-dimethyl-N-cyclohexyl-N-2-hydroxypropylammonium pivalate (molecular weight: 287), expressed by formula [1e] above, was added. When a total of 2.5 g (143 ppm) of catalyst solution was added, a reaction started and was continued at a temperature of 60° C. When the refractive index of the reaction mixture reached 1.4625, 2.7 g of a 6.8% -xylol solution of monochloroacetic acid was added to terminate the reaction. The cooled reaction mixture had a light color with a Hazen color unit of 10 to 20.

Subsequently, a 1,000 g aliquot of the reaction mixture was subjected to molecular distillation to obtain 249.7 g (conversion: 25.0%) of the sought polyisocyanate as a reaction residue and, on the other hand, 749.9 g (recovery ratio 75.0%) of HDI as a distillate.

The resulting polyisocyanate (P-3) solution had a light color (Hazen color unit 40), Gardner viscosity of W, and NCO% of 23.3.%. The polyisocyanate (P-3) was confirmed to be an isocyanurate-type polyisocyanate, containing 72% of the mononuclear polyisocyanate group with a number-average molecular weight of 550 (as determined through the same instrument analysis as in Example 1).

The polyisocyanate (P-3) indicated good compatibility with each of acrylic polyol: "ACRYDIC A-801" and the trial-made acrylic polyol (B).

EXAMPLE 4

The same procedure as described in Example 1 was performed except for the following. As the isocyanuration catalyst, a 20%-butyl Cellosolve solution of N,N-dimethyl-N-cyclohexyl-N-2-hydroxypropylammonium 2-methyl-2-ethyl-butanoate (molecular weight 315), expressed by formula [1h] above, was added. When a total of 2.2 g (126 ppm) of catalyst solution was added, a reaction started and was continued at a temperature of 60° C. When the refractive index of the reaction mixture reached 1.4625, 2.2 g of a 6.8%-xylol solution of monochloroacetic acid was added to terminate the reaction. The resulting cooled reaction mixture had a light color, indicating a Hazen color unit of 10 to 12.

Subsequently, a 1,000 g aliquot of the reaction mixture was subjected to molecular distillation to obtain 249.5 g (conversion: 25.0%) of the sought polyisocyanate as a reaction residue and, on the other hand, 749.6 g (recovery ratio 75.0%) of HDI as a distillate.

The resulting polyisocyanate (P-4) solution had a light color (Hazen color unit 40), Gardner viscosity of W, and NCO% of 23.0. The polyisocyanate (P-4) was confirmed to be an isocyanurate-type polyisocyanate, containing 72% of the mononuclear polyisocyanate group with a number-average molecular weight of 550 (as determined through the same instrument analysis as in Example 1).

The polyisocyanate (P-4) indicated good compatibility with each of acrylic polyol: "ACRYDIC A-801" and trial-made acrylic polyol (B).

EXAMPLE 5

The same procedure as described in Example 1 was performed except for the following. As the isocyanuration catalyst, a 20%-butyl Cellosolve solution of N,N-dimethyl-N-cyclohexyl-N-2-hydroxypropylammonium 2.2-dimethylpentanoate (molecular weight: 315), expressed by formula [1i] above, was added. When a total of 1.9 g (109 ppm) of catalyst solution was added, a reaction started and was continued at a temperature of 60° C. When the refractive index of the reaction mixture reached 1.4625, 2.2 g of a 6.8%-xylol solution of monochloroacetic acid was added to terminate the reaction. The resulting cooled reaction mixture had a light color, indicating a Hazen color unit of 10.

Subsequently, a 1,000 g aliquot of the reaction mixture was subjected to molecular distillation to obtain 249.8 g (conversion: 25.0%) of the sought polyisocyanate as a reaction residue and, on the other hand, 749.2 g (recovery ratio: 75.0%) of HDI as a distillate.

The resulting polyisocyanate (P-5) solution had a light color (Hazen color unit 30), Gardner viscosity of W, and NCO% of 23.2%. The polyisocyanate (P-5) was confirmed to be an isocyanurate-type polyisocyanate, containing 71% of the mononuclear polyisocyanate group with a number-average molecular weight of 550 (as determined through the same instrument analysis as in Example 1).

The polyisocyanate (P-5) indicated good compatibility with each of acrylic polyol: "ACRIDIC A-801" and trial-made acrylic polyol (B).

EXAMPLE 6

The same procedure as described in Example 1 was performed except for the following. As the isocyanuration catalyst, 2.0 g (114 ppm) of a 20%-butyl Cellosolve solution of [1b] (same solution as used in Example 1) consisting of 2,800 g of hexamethylene diisocyanate (HDI) and 700 g of 1,3-bis(isocyanatomethyl)cyclohexane (H6XDI) as raw material was used to promote reaction in the system. When the refractive index of the reaction mixture reached 1.4690, 2.8 g of a 6.85-xylol solution of monochloroacetic acid was used to deactivate the reaction. The resulting reaction mixture had a light color, indicating a Hazen color unit of 10 to 12.

Subsequently, a 1,000 g aliquot of the reaction mixture was subjected to molecular distillation to obtain 258.7 g (conversion: 26.0%) of the sought polyisocyanate as a reaction residue and, on the other hand, 736.3 g (recovery ratio: 74%) of HDI as a distillate.

The resulting polyisocyanate (P-6) solution had a light color (Hazen color unit 30) and NCO% of 22.5%. The polyisocyanate (P-6) was confirmed to be an isocyanurate-type polyisocyanate consisting of HDI and H6XDI, containing 71% of the mononuclear polyisocyanate group with a number-average molecular weight of 570 (as determined through the same instrument analysis as in Example 1).

The polyisocyanate (P-6) indicated good compatibility with each of acrylic polyol: "ACRYDIC A-801" and trial-made acrylic polyol (B). When the clear varnish prepared by the equivalent mixture ratio was coated on a glass plate, a very cohesive, cured film was obtained.

EXAMPLE 7

The same procedure as described in Example 1 was performed except for the following. As the isocyanuration catalyst, 0.72 g (41 ppm) of a 20%-butyl Cellosolve solution of [1b] (same solution as used in Example 1) consisting of 3,500 g of hexamethylene diisocyanate (HDI) and 125 g of 2,2,4-trimethyl-1,3-pentanediol (TMPD) as raw materials was used to promote reaction in the system. When the refractive index of the reaction mixture reached 1.4662, 1.0 g of a 6.8%-xylol solution of monochloroacetic acid was used to deactivate the reaction. The resulting reaction mixture had a light color, indicating a Hazen color unit of less than 10.

Subsequently, a 1,000 g aliquot of the reaction mixture was subjected to molecular distillation to obtain 342.9 g (conversion: 34.5%) of the sought polyisocyanate as a reaction residue and, on the other hand, 651.1 g (recovery ratio: 65.5%) of HDI as a distillate.

The resulting polyisocyanate (P-7) solution had a light color (Hazen color unit 20) and NCO% of 20.8%. The polyisocyanate (P-7) was confirmed to be a diol-modified isocyanurate-type polyisocyanate having isocyanurate rings and an adduct of TMPD with a number-average molecular weight of 620 (as determined through the same instrument analysis as in Example 1).

The polyisocyanate (P-7) indicated good compatibility with each of acrylic polyol: "ACRIDIC A-801" and the trial-made acrylic polyol (B). When the clear varnish prepared by the equivalent mixture ratio was coated and left on a glass plate, a very cohesive, cured film was obtained.

COMPARATIVE EXAMPLE 1

In the same process as described in Example 1, a 20%-butyl Cellosolve solution of well-known N,N,N,-trimethyl-N-2-hydroxypropylammonium octanoate (molecular weight: 271; ref. Patent Publication (Kokai)No. 55-143978) was used as the isocyanuration catalyst. The solution was added in portions. When the total added amount became 7.9 g (451 ppm), a reaction started Continuing the reaction at a temperature of 60° C. until the refractive index of the reaction mixture reached 1.4625, 8.6 g of a 6.8%-xylol solution of monochloroacetic acid was added to terminate the reaction. The resulting cooled reaction mixture was colored, indicating a Hazen color unit of 220.

Subsequently, a 1,000 g aliquot of the reaction mixture was subjected to molecular distillation to obtain 248.9 g (conversion 24.9%) of the sought polyisocyanate as a reaction residue, and 750.1 g (recovery ratio 75.0%) of HDI as a distillate.

The resulting polyisocyanate (S-1) solution was colored, indicating a Hazen color unit of 340 to 360, Gardner viscosity of W, and NCO% of 22.9%. The polyisocyanate (S-1) was confirmed to be an isocyanurate-type polyisocyanate containing 68% of a polyisocyanate ring with a number-average molecular weight of 580 (as determined through the same instrument analysis as in Example 1).

The polyisocyanate (S-1) indicated good compatibility with acrylic polyol "ACRYDIC A-801" and the trial-made acrylic polyol (B), but the quality was poor due to excessive coloration.

COMPARATIVE EXAMPLE 2

In the same process as described in Example 1, a 20%-butyl Cellosolve solution of well-known N,N,N- trimethyl-N-2-hydroxypropylammonium p-t-butylbenzoate (molecular weight: 295; ref. Patent Publication (Kokai) No. 60-181078) was used as the isocyanuration catalyst. The solution was added in portions. When the total added amount became 5.2 g (297 ppm), a reaction started. Due to slow reaction at 60° C., 0.8 g (46 ppm) of the catalyst solution was added to promote the reaction. When the refractive index of the reaction mixture reached 1.4625, 6.0 g of a 6.8%-xylol solution of monochloroacetic acid was added to terminate the reaction. The resulting cooled reaction mixture was colored, indicating a Hazen color unit of 160.

Subsequently, a 1,000 g aliquot of the reaction mixture was subjected to molecular distillation to obtain 249.3 g (conversion: 25.0%) of the sought polyisocyanate as a reaction residue, on the other hand, and 749.8 g (recovery ratio: 75.0%) of HDI as a distillate.

The resulting polyisocyanate (S-2) solution was colored, indicating a Hazen color unit of 260, viscosity of X, and NCO% of 22.8. The polyisocyanate (S-2) was confirmed to be an isocyanurate-type polyisocyanate containing 68% of a isocyanurate ring with a number-average molecular weight of 580 (as determined through instrument analysis).

The polyisocyanate (S-2) indicated good compatibility with acrylic polyol "ACRIDIC A-801" and the trial-made acrylic polyol (B), but the quality was poor due to excessive coloration.

What is claimed is:

1. A process for preparing an isocyanurate-type polyisocyanate which comprises reacting an aliphatic or alicyclic diisocyanate compound comprising hexamethylene diisocyanate as a major component in the presence of an isocyanuration catalyst represented by general formula,

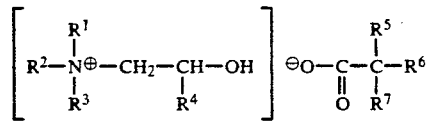

wherein $R^1$, $R^2$ and $R^3$ independently represent a hydrocarbon group containing 1 to 20 carbon atoms, or a hydrocarbon group containing one or more hetero atoms; or wherein $R^1$, $R^2$ and $R^3$ each represent a hydrocarbon group and two of $R^1$, $R^2$ and $R^3$ are linked to each other to form a piperidine or a morpholine ring; $R^4$ indicates a hydrogen atom or a hydrocarbon group containing 1 to 20 carbon atoms; and $R^5$, $R^6$ and $R^7$ independently represent a hydrocarbon group containing 1 to 20 carbon atoms.

2. A process for preparing a diol-modified isocyanurate-type polyisocyanate which comprises reacting an aliphatic or alicyclic diisocyanate compound comprising hexamethylene diisocyanate as a major component in the presence of (a) an isocyanuration catalyst represented by general formula,

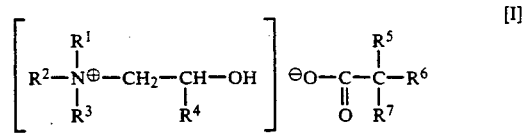

wherein $R^1$, $R^2$ and $R^3$ independently represent a hydrocarbon group containing 1 to 20 carbon atoms, or a hydrocarbon group containing one or more hetero atoms; or wherein $R^1$, $R^2$ and $R^3$ each represent a hydrocarbon group and two of $R^1$, $R^2$ and $R^3$ are linked to each other to form a piperidine or a morpholine ring; $R^4$ indicates a hydrogen atom or a hydrocarbon group containing 1 to 20 carbon atoms; and $R^5$, $R^6$ and $R^7$ independently represent a hydrocarbon group containing 1 to 20 carbon atoms, and (b) a hydrocarbon diol.

3. A process as claimed in claim 1, wherein said isocyanurate catalyst is used in an amount of from 20 to 200 ppm based on the weight of the diisocyanate compound charged.

4. A process as claimed in claim 1, wherein said aliphatic diisocyanate compound is at least one compound selected from the group consisting of 2,2,4-trimethylhexamethylene diisocyanate and dodecamethylene diisocyanate.

5. A process as claimed in claim 1, wherein said alicyclic diisocyanate compound is at least one compound selected from the group consisting of 1,4-cyclohexanediisocyanate, and 1,3-bis(isocyanatomethyl)cyclohexane.

6. A process as claimed in claim 1, wherein said isocyanurate-type polyisocyanate contains at least 65% by weight of a mononuclear polyisocyanate.

7. A process as claimed in claim 2, wherein said isocyanurate catalyst is used in an amount of from 20 to 200 ppm based on the weight of the diisocyanate compound charged.

8. A process as claimed in claim 2, wherein said aliphatic diisocyanate compound is at least one compound selected from the group consisting of 2,2,4-trimethylhexamethylene diisocyanate and dodecamethylene diisocyanate.

9. A process as claimed in claim 2, wherein said alicyclic diisocyanate compound is at least one compound selected from the group consisting of 1,4-cyclohexanediisocyanate, and 1,3-bis(isocyanatomethyl)cyclohexane.

10. A process as claimed in claim 2, wherein said isocyanurate-type polyisocyanate contains at least 65% by weight of a mononuclear polyisocyanate.

* * * * *